United States Patent [19]
Arzeno et al.

[11] Patent Number: 6,103,901
[45] Date of Patent: Aug. 15, 2000

[54] PROCESS FOR PREPARING A 2-(2-AMINO-1, 6-DIHYDRO-6-OXO-PURIN-9-YL)METHOXY-1,3-PROPANEDIOL DERIVATIVE

[75] Inventors: Humberto B. Arzeno, Cupertino; Eric R. Humphreys, San Bruno, both of Calif.; Jim-Wah Wong, Boulder; Christopher R. Roberts, Berthoud, both of Colo.

[73] Assignee: Syntex (U.S.A.) Inc., Palo Alto, Calif.

[21] Appl. No.: 09/121,446

[22] Filed: Jul. 23, 1998

Related U.S. Application Data

[60] Division of application No. 08/775,424, Jan. 9, 1997, Pat. No. 5,840,890, which is a continuation-in-part of application No. 08/592,282, Jan. 26, 1996, abandoned.

[51] Int. Cl.⁷ .......................... C07D 473/18; C07B 51/00
[52] U.S. Cl. .............................................................. 544/276
[58] Field of Search ............................................. 544/276

[56] References Cited

U.S. PATENT DOCUMENTS

| | | | |
|---|---|---|---|
| 4,355,032 | 10/1982 | Verheyden et al. | 424/253 |
| 5,043,339 | 8/1991 | Beauchamp | 514/274 |

FOREIGN PATENT DOCUMENTS

| | | |
|---|---|---|
| 0 158 847 | 10/1985 | European Pat. Off. |
| 0 308 065 | 3/1989 | European Pat. Off. |
| 0 375 329 | 6/1990 | European Pat. Off. |
| 1 523 865 | 6/1978 | United Kingdom |
| 2 122 618 | 1/1984 | United Kingdom |
| 2 104 070 | 3/1984 | United Kingdom |
| 8829571 | 6/1990 | United Kingdom |
| WO 94/29311 | 12/1994 | WIPO |

OTHER PUBLICATIONS

E. Jensen et. al., *Acta Pharm. Nord.* 3(4) 243–247 (1991).
John C. Martin et. al., *J. Pharm. Sci.* 76(2), p. 180–184 (1987).
P.C. Maudgal et. al., *Arch. Ophthalmol.* 1984; 102: 140–142.
Leon Colla et. al., *J. Med. Chem.* 98, 3, 26, 602–604 (1983).
L. M. Beauchamp et. al., *Antiviral Chemistry & Chemotherapy* (1992), 3 (3), 157–164.

*Primary Examiner*—Mark L. Berch
*Attorney, Agent, or Firm*—Heller Ehrman White & McAuliffe LLP

[57] ABSTRACT

Intermediates of Formula (III)

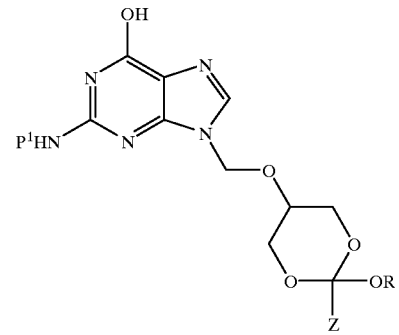

wherein $P^1$ is hydrogen or an amino-protecting group, R is lower alkyl, allyl or aralkyl, and Z is hydrogen, lower alkyl, aryl or aralkyl; and Formula (VI)

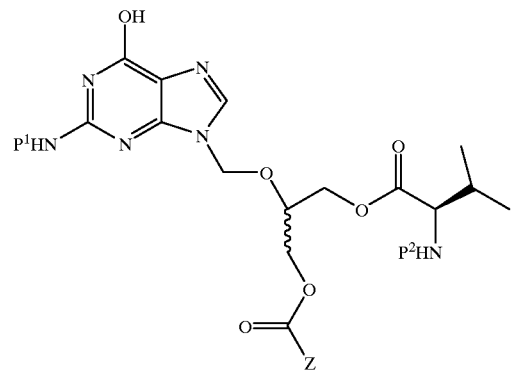

wherein $P^1$ is hydrogen or an amino-protecting group, $P^2$ is an amino protecting group, and Z is hydrogen, lower alkyl, aryl or aralkyl, are useful in a novel process for preparing the mono-L-valine ester of 2-(2-amino-1,6-dihydro-6-oxo-purin-9-yl)methoxy-1,3-propanediol (ganciclovir). The mono-L-valine ester of ganciclovir and its pharmaceutically acceptable salts are of value as antiviral agents with improved absorption.

2 Claims, No Drawings

PROCESS FOR PREPARING A 2-(2-AMINO-1, 6-DIHYDRO-6-OXO-PURIN-9-YL)METHOXY- 1,3-PROPANEDIOL DERIVATIVE

CROSS-REFERENCE TO RELATED APPLICATIONS

This application is a division of application Ser. No. 08/775,424, filed Jan. 9, 1997, U.S. Pat. No. 5,840,890 which is in turn a continuation-in-part of application Ser. No. 08/592,282, filed Jan. 26, 1996, now abandoned.

BACKGROUND OF THE INVENTION

1. Field of the Invention

The present invention relates to a process for preparing a prodrug formulation of ganciclovir and its pharmaceutically acceptable salts. More specifically, the invention relates to a process for preparing the mono-L-valine ester derived from 2-(2-amino-1,6-dihydro-6-oxo-purin-9-yl)methoxy-1,3-propanediol and its pharmaceutically acceptable salts. The invention also relates to novel intermediates useful in the above process and to a process for preparing those intermediates.

2. Background Information

British Patent 1 523 865 describes antiviral purine derivatives with an acyclic chain in the 9-position. Among those derivatives 2-(2-amino-1,6-dihydro-6-oxo-purin-9-yl) methoxy-ethanol with the INN name acyclovir has been found to have good activity against herpes viruses such as herpes simplex.

U.S. Pat. No. 4,355,032 discloses the compound 9-[(2-hydroxy-1-hydroxy-methylethoxy)methyl]guanine or 2-(2-amino-1,6-dihydro-6-oxo-purin-9-yl)-methoxy-1,3-propanediol with the INN name ganciclovir. Ganciclovir is highly efficacious against viruses of the herpes family, for example, against herpes simplex and cytomegalovirus.

European Patent Application 0 375 329 A2 discloses prodrug compounds with the following formula

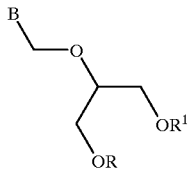

wherein R and $R^1$ are independently selected from hydrogen and an amino acid acyl residue, provided at least one of R and $R^1$ represents an amino acid acyl residue and B represents a group of the formulae

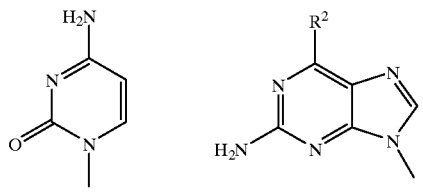

in which $R^2$ represents a $C_{1-6}$ straight chain, $C_{3-6}$ branched chain or $C_{3-6}$ cyclic alkoxy group, or a hydroxy or amino group or a hydrogen atom and the physiologically acceptable salts thereof. These prodrug compounds are described as having advantageous bioavailability when administered by the oral route, resulting in high levels of the parent compound in the body.

Example 3(b) of European Patent Application 0 375 329 A2 discloses the preparation of the bis-(L-isoleucinate) ester of ganciclovir as a white foam. Example 4(b) discloses the preparation of the bis(glycinate) ester of ganciclovir as a white solid. Example 5(b) discloses the preparation of the bis-(L-valinate) ester of ganciclovir as a solid. Example 6(b) discloses the preparation of the bis-(L-alaninate) ester of ganciclovir as a syrup containing 90% of the bis ester and 10% of the monoester. The bis-esters are prepared by reacting ganciclovir with an optionally protected amino acid or functional equivalent thereof. The reaction may be carried out in a conventional manner, for example in a solvent such as pyridine, dimethylformamide, etc., in the presence of a coupling agent such as 1,3-dicyclohexylcarbodiimide, optionally in the presence of a catalytic base such as 4-dimethylaminopyridine. The described bis esters are non-crystalline materials which are difficult to process for the manufacture of oral pharmaceutical dosage forms.

British Patent Application No. 8829571 is the priority patent application for European Patent Application 0 375 329 A2 and U.S. Pat. No. 5,043,339, and discloses amino acid esters of the compounds of the formula

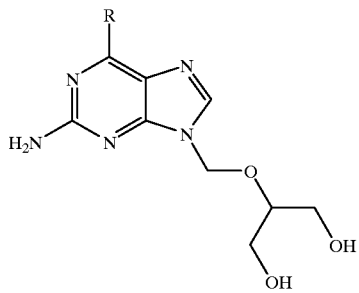

(wherein R represents a hydroxy or amino group or a hydrogen atom) and the physiologically acceptable salts thereof. Examples of preferred amino acids include aliphatic acids e.g. containing up to 6 carbon atoms such as glycine, alanine, valine and isoleucine. The amino acid esters include both mono and diesters. The preparation of the diesters is identical to the preparation in European Patent Application 0 375 329 A2; however, this patent application as well as European Patent Application 0 375 329 A2 and U.S. Pat. No. 5,043,339 do not disclose the preparation of monoesters, or any data suggesting their usefulness.

Leon Colla et al., J. Med. Chem. (1983) 26, 602–604, disclose several water-soluble ester derivatives of acyclovir and their salts as prodrugs of acyclovir. The authors indicate that acyclovir cannot be given as eye drops or intramuscular injections because of its limited solubility in water and have therefore synthesized derivatives of acyclovir which are more water soluble than the parent compound. The authors disclose the hydrochloride salt of the glycyl ester, the hydrochloride salt of the alanyl ester, the hydrochloride salt of the beta-alanyl ester, the sodium salt of the succinyl ester, and the azidoacetate ester. The alanyl esters were prepared by conventional esterification methods, including reacting acyclovir with the corresponding N-carboxy-protected amino acid in pyridine, in the presence of 1,3-dicyclohexylcarbodiimide and a catalytic amount of p-toluenesulfonic acid and subsequent catalytic hydrogenation to give the alpha- and beta-alanyl esters as their hydrochloride salts.

L. M. Beauchamp et al., Antiviral Chemistry & Chemotherapy (1992), 3 (3), 157–164, disclose eighteen amino acid esters of the antiherpetic drug acyclovir and their effectiveness as prodrugs of acyclovir, evaluated in rats by measuring the urinary recovery of acyclovir. Ten prodrugs produced greater amounts of the parent drug in the urine than acyclovir itself: the glycyl, D,L-alanyl, L-alanyl, L-2-aminobutyrate, D,L-valyl, L-valyl, DL-isoleucyl, L-isoleucyl, L-methionyl, and L-prolyl ester. According to the authors, the L-valyl ester of acyclovir was the best prodrug of the esters investigated. These esters were prepared by methods similar to those employed by Colla et al.

European Patent Application 0 308 065 A2 discloses. the valine and isoleucine esters of acyclovir, preferably in the L-form, as showing a large increase in absorption from the gut after oral administration, when compared with other esters and acyclovir. The amino acid esters are prepared by conventional esterification methods, including reacting acyclovir with an N-carboxy-protected amino acid or an acid halide or acid anhydride of the amino acid, in a solvent such as pyridine or dimethylformamide, optionally in the presence of a catalytic base.

PCT Patent Application WO 94/29311 discloses a process for the preparation of amino acid esters of a nucleoside analogue, including acyclovir and ganciclovir. This process comprises reacting a nucleoside analogue having an esterifiable hydroxy group in its linear or cyclic ether moiety, with a 2-oxa-4-aza-cycloalkane-1,3-dione of the formula

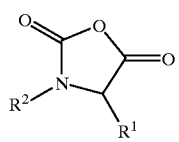

wherein $R^1$ may represent hydrogen, a $C_{1-4}$ alkyl or alkenyl group or other amino acid side chains, and $R^2$ may represent hydrogen or a group $COOR^3$ where $R^3$ is a benzyl, t-butyl, fluorenylmethyl or an optionally halo substituted linear or branched $C_{1-8}$ alkyl group. Preferred $R^1$ groups include hydrogen, methyl, isopropyl and isobutyl, yielding respectively the glycine, alanine, valine and isoleucine esters of acyclovir or ganciclovir.

Examples 1–3 of PCT Patent Application WO 94/29311 disclose only the condensation of acyclovir with the valine-substituted 2-oxa-4-aza-cycloalkane-1,3-dione (Z-valine-N-carboxyanhydride) by conventional procedures. While the amino acid esters of the PCT application include both the acyclovir and ganciclovir [9-((1,3-dihydroxy-2-propoxy) methyl)-guanine or DHPG]esters, the application does not disclose how to prepare the ganciclovir esters, much less the mono-esters of ganciclovir. The mono-L-valine ester derived from 2-(2-amino-1,6-dihydro-6-oxo-purin-9-yl)-methoxy-1,3-propanediol and its pharmaceutically acceptable salts are potent antiviral agents and are described in European Patent Application 0 694 547 A. These compounds have been found to have improved oral absorption and low toxicity. This patent application also discloses certain processes for preparing these esters, different from those described herein.

The present invention relates to an improved process whereby a cyclic orthoester, a monocarboxylate and a monocarboxylate-monovalinate of ganciclovir are prepared as intermediates. The monocarboxylate intermediate is formed with high selectivity and in high yields, and provides for mono-esterification by an L-valine derivative. The monocarboxylate-monovalinate can then be selectively hydrolyzed to the monovaline ester which is obtained in good yield and purity.

SUMMARY OF THE INVENTION

In a first aspect, this invention provides a process for preparing the compound of Formula (I)

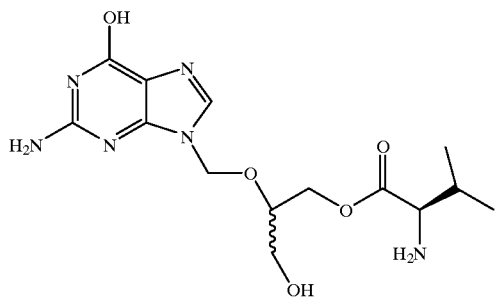

and pharmaceutically acceptable salts thereof, which compound is named hereinafter 2-(2-amino-1,6-dihydro-6-oxo-purin-9-yl)methoxy-3-hydroxy-1-propyl-L-valinate or mono-L-valine ganciclovir.

This process involves the transesterification of an orthoester of Formula (II), Z—C(OR)$_3$, wherein R is lower alkyl, allyl or aralkyl, and Z is hydrogen, lower alkyl, aryl or aralkyl, with ganciclovir to give the corresponding cyclic orthoester of ganciclovir of Formula (III)

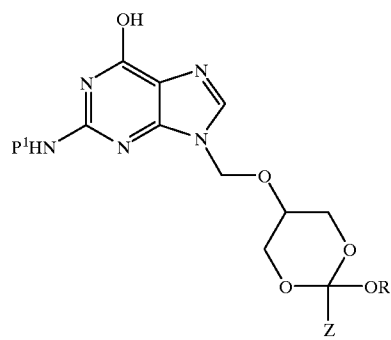

wherein $P^1$ is hydrogen or an amino protecting group, R is lower alkyl, allyl or aralkyl, and Z is hydrogen, lower alkyl, aryl or aralkyl, followed by the formation of ganciclovir monocarboxylate of Formula (IV))

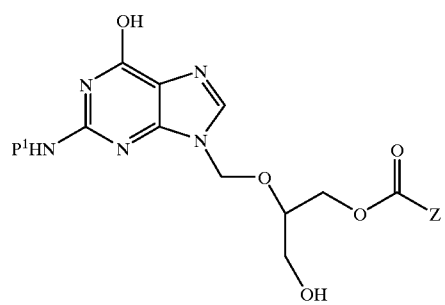

wherein $P^1$ is hydrogen or an amino protecting group, and Z is hydrogen, lower alkyl, aryl or aralkyl.

This product is then esterified with an L-valine derivative of Formula (V)

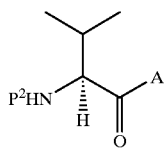

wherein P² is an amino-protecting group and A is a carboxy-activating group, to provide a monocarboxylate-monovalinate of ganciclovir of Formula (VI)

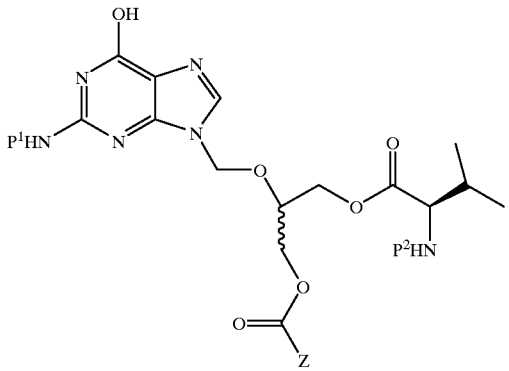

wherein P¹ is hydrogen or an amino protecting group, P² is an amino protecting group, and Z is hydrogen, lower alkyl, aryl or aralkyl, followed by removal of the acyl (e.g., alkanoyl or phenylacetyl) group by selective hydrolysis and, finally, removal of any protecting groups to yield the prodrug of Formula (I). Optionally, the process can also include the formation of salts of the prodrug of Formula (I), the conversion of an acid addition salt of the prodrug of Formula (I) into a non-salt form, the optical resolution of a compound of Formula (I), or the preparation of the prodrugs of Formula (I) in crystalline form. Details of the process are described below.

In a second aspect, this invention provides a novel enzymatic hydrolysis in which the monocarboxylate-monovalinate intermediate of Formula (VI) is selectively hydrolyzed via enzymatic catalysis to the monovalinate of Formula (VII)

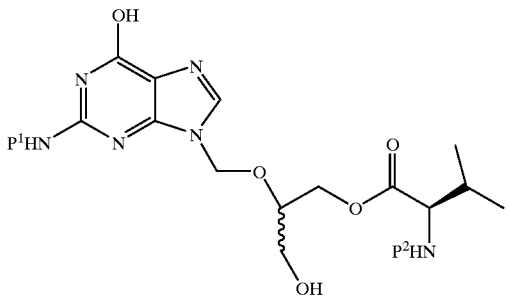

wherein P¹ is hydrogen or an amino protecting group and P² is an amino protecting group.

In a third aspect, this invention provides compounds of Formulae (III), (IV) and (VI) which are useful intermediates for preparing mono-L-valine ganciclovir and their pharmaceutically acceptable salts.

In a fourth aspect, this invention provides processes for preparing the intermediates of Formulae (III), (IV) and (VI).

DETAILED DESCRIPTION OF THE INVENTION

Definitions

Unless otherwise stated, the following terms used in the specification and claims have the meanings given below:

"BOC" means t-butoxycarbonyl.

"CBZ" means carbobenzyloxy (benzyloxycarbonyl).

"FMOC" means N-(9-fluorenylmethoxycarbonyl).

"DHPG" means 9-[(1,3-dihydroxy-2-propoxy)methyl] guanine.

"Alkyl" means a straight or branched saturated hydrocarbon radical having from one to the number of carbon atoms designated. For example, $C_{1-7}$ alkyl is alkyl having at least one but no more than seven carbon atoms, e.g. methyl, ethyl, i-propyl, n-propyl, n-butyl, n-pentyl, n-heptyl and the like.

"Lower alkyl" means an alkyl group of one to six carbon atoms.

"Allyl" means an unsaturated organic radical $C_3H_5$, such as $—CH_2—CH=CH_2$, $—CH=CH—CH_3$, or $—C(CH_3)=CH_2$.

"Acyl" means an organic radical derived from an organic acid by the removal of the hydroxyl group; e.g., $CH_3CO—$ is the acyl radical of $CH_3COOH$, or acetyl. Other examples for such acyl groups are propionyl, or benzoyl, etc. The term "acyl" includes the term "alkanoyl" which is the organic radical RCO— in which R is an alkyl group as defined above.

"Lower alkoxy", "(lower alkyl)amino", "di(lower alkyl) amino", "(lower alkanoyl)amino", and similar terms mean alkoxy, alkylamino, dialkylamino, alkanoylamino, etc. in which the or each alkyl radical is a "lower alkyl" as described above.

"Aprotic polar solvent" refers to organic solvents which may be either water-immiscible, such as halogenated hydrocarbons, e.g. methylene chloride, chloroform, etc., or water-miscible, such as tetrahydrofuran, dimethoxyethane, bis(2-methoxyethyl)ether (diglyme), dimethylformamide, N-methylpyrrolidone, dimethylsulfoxide, etc.

"Aryl" means an organic radical derived from an aromatic hydrocarbon by the removal of one hydrogen atom. Preferred aryl radicals are aromatic carbocyclic radicals having a single ring (e.g., phenyl) or two condensed rings (e.g., naphthyl). Most preferred is the phenyl radical $C_6H_5—$.

"Aralkyl" means an organic radical derived from an alkyl in which a hydrogen atom is substituted by an above-defined aryl group; e.g., benzyl, phenylethyl, phenylpropyl, and the like.

"Benzyl" is the radical $PhCH_2—$, derived from toluene.

"Benzoyl" refers to the radical Ph—CO— where Ph— is the phenyl radical $C_6H_5—$.

"Halogen" or "halo" means fluorine, chlorine, bromine, or iodine.

"Derivative" of a compound means a compound obtainable from the original compound by a simple chemical process.

"Activated derivative" of a compound means a reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance and corresponding activating agents or groupings which activate the carboxy group are described in more detail below. An example of an activated derivative of L-valine is the compound of Formula (V)

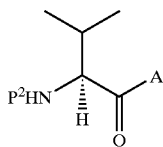

wherein P² is an amino-protecting group and A is a carboxy-activating group, for example, halo, a lower acyloxy group, a carbodiimide derived group, such as from 1-ethyl-3-(3-dimethylaminopropyl)carbodiimide (EDAC), an isobutyrate group, and the like. Of particular interest for the present invention is an amino acid anhydride which is an activated form of an amino acid which renders the amino acid (especially L-valine) susceptible to esterification. Amino acid anhydrides are included in the compounds of Formula (V), above. Especially useful for the present invention are the cyclic amino acid anhydrides of L-valine, described in PCT Patent Application WO 94/29311, such as 2-oxa-4-aza-5-isopropyl-cycloalkane-1,3-dione of Formula (Va):

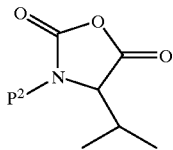

in which P² is an amino protecting group. Other examples of the cyclic amino acid anhydrides are protected amino acid N-carboxy anhydrides (NCA's) described in more detail below.

"Orthoesters" are compounds of Formula (II), Z—C(OR)₃, wherein R is lower alkyl, allyl or aralkyl, and Z is hydrogen, lower alkyl, aryl or aralkyl. These compounds are well-known. Some of the more common orthoesters, such as trimethyl and/or triethyl orthoformate, orthoacetate, orthopropionate, orthobutyrate, orthovalerate and orthobenzoate are commercially available, e.g., from Aldrich Chemical Company, Milwaukee, Wis.

"Orthoformate" is a compound of Formula (II), Z—C(OR)₃ wherein Z is hydrogen and R is alkyl of 1–6 carbon atoms, allyl or aralkyl. These compounds are well-known. A convenient synthesis of these compounds is described in E. R. Alexander et al., J. Amer. Chem. Soc. 74, 554(1952).

"Alkanoic acid" refers to an organic acid of Formula R—COOH where R is lower alkyl of 1–6 carbon atoms.

"Alkanoate" means an ester of an alkanoic acid as defined above, i.e., R—COOR'.

"Alkanoyl" refers to the radical R—CO— where R is lower alkyl.

"Transesterification" means the conversion of an organic acid ester into another ester of the same acid. The ester interchange takes place when the ester is treated with an alcohol, usually in the presence of an acid or base.

"Protecting group" means a chemical group that (a) preserves a reactive group from participating in an undesirable chemical reaction; and (b) can be easily removed after protection of the reactive group is no longer required. For example, the benzyl group is a protecting group for a primary hydroxyl function.

"Amino-protecting group" means a protecting group that preserves a reactive amino group that otherwise would be modified by certain chemical reactions. The definition includes the acetyl group or lower alkanoyl groups with 2 to 4 carbon atoms, in particular the acetyl or propionyl group, the trityl or substituted trityl groups, such as the monomethoxy-trityl group, dimethoxytrityl groups such as 4,4'-dimethoxytrityl, the phthalyl group, the silyl group, the trichloroacetyl group, the trifluoroacetyl group, and the N-(9-fluorenylmethoxycarbonyl) or "FMOC" group, the allyloxycarbonyl group or other protecting groups derived from halocarbonates such as (C₆–C₁₂)aryl lower alkyl carbonates (such as the N-benzyloxycarbonyl group derived from benzylchlorocarbonate), or derived from biphenylalkyl halocarbonates, or tertiary alkyl halo- carbonates, such as tertiary butylhalocarbonates, in particular t-butyl chlorocarbonate, or di(lower)alkyl dicarbonates, in particular di(t-butyl) dicarbonate, and triphenylmethyl halides such as triphenylmethyl chloride, and trifluoroacetic anhydride.

"Trityl" means the triphenylmethyl radical (Ph)₃C—.

"Leaving group" means a labile group that is replaced in a chemical reaction by another group. Examples of leaving groups are halogen, the optionally substituted benzyloxy group, the isopropyloxy group, the mesyloxy group, the tosyloxy group or the acyloxy group.

All the activating and protecting agents employed in the preparation of the compound of Formula (I) must meet the following qualifications: (1) their introduction should proceed quantitatively and without racemization of the L-valine component; (2) the protecting group present during the desired reaction should be stable to the reaction conditions to be employed; and (3) the group must be readily removable under conditions in which the ester bond is stable and under which racemization of the L-valine component of the ester does not occur.

The process of the invention may also include the optical resolution of a prodrug of Formula (I). Terminology relating to the stereochemistry and optical resolution of these compounds is described in EP A 0694 547, incorporated herein by reference.

"Optional" or "optionally" means that a described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution;

"optionally followed by converting the free base to the acid addition salt" means that said conversion may or may not be carried out in order for the process described to fall within the invention, and the invention includes those processes wherein the free base is converted to the acid addition salt and those processes in which it is not.

"Pharmaceutically acceptable" means that which is useful in preparing a pharmaceutical composition that is generally safe and non-toxic and includes that which is acceptable for veterinary use as well as human pharmaceutical use.

"Pharmaceutically acceptable salts" means salts which possess the desired pharmacological activity and which are neither biologically nor otherwise undesirable. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylene-bis(3-hydroxy-2-naphthoic)acid, 3-phenylpropionic acid, trimethylacetic acid, t-butylacetic acid, lauryl sulfuric acid, gluconic acid, glutamic acid, hydroxy-naphthoic acids, salicylic acid, stearic acid, muconic acid, and the like. Preferred pharmaceutically acceptable salts are those formed with hydrochloric acid, sulfuric acid, phosphoric acid, acetic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid and camphorsulfonic acid.

"Enzymatic hydrolysis" means the hydrolysis of an ester, e.g., an alkanoate such as acetate or propionate, or an aralkanoate such as benzoate, by enzymatic action. The choice of a suitable enzyme is dependent on the structure of the substituent of Z in compound VI, e.g., for Z=lower alkyl, aryl or aralkyl, suitable enzymes are found in the classes of enzymes with EC numbers 3.1.1.1., 3.1.1.3. and 3.1.1.6. For Z=benzyl, a suitable enzyme would be penicillin acylase, EC number 3.5.1.1. A further restriction criterion would be selectivity for non-hydrolysis of the valine ester moiety. Suitable enzyme preparation are, for example, pig liver esterase, available from Sigma Chemical Co., St. Louis, Mo.; Amano AK, a pseudomonas species lipase, available in crude form from Amano International, Troy, Va.; or in purified form as Chiro-CLEC® PC, an enzyme polymer available from Altus Biologics Inc., Cambridge, Mass.

Synthetic Reaction Parameters

Unless specified to the contrary, the reactions described herein take place at atmospheric pressure within a temperature range from 5° C. to 170° C. (preferably from 10° C. to 50° C.; most preferably at "room" or "ambient" temperature, e.g., about 20°–30° C.). However, there are clearly some reactions where the temperature range used in the chemical reaction will be above or below these temperature ranges. Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20°–30° C.) over a period of about 1 to about 100 hours (preferably about 5 to 60 hours). Parameters given in the Examples are intended to be specific, not approximate. For chemical reactions that take plate at elevated pressures, e.g., hydrogenation/hydrogenolysis reactions, the pressure is given in psi or atm units and indicates pressure above normal or atmospheric pressure.

Isolation and purification of the compounds and intermediates described herein can be effected, if desired, by any suitable separation or purification procedure, such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Presently Preferred Embodiments

While the broadest definition of this invention is set forth in the Summary of the Invention as a process for preparing the compound of Formula (I) and its pharmaceutically acceptable salts, the (R,S) mixture and certain salts are preferred.

The following acids are preferred to form pharmaceutically acceptable salts with the compound of Formula (I): hydrochloric, sulfuric, phosphoric acid, acetic, methanesulfonic, ethanesulfonic, 1,2-ethanedisulfonic, 2-hydroxyethanesulfonic, benzenesulfonic, p-chlorobenzenesulfonic, 2-naphthalenesulfonic, p-toluenesulfonic and camphorsulfonic acid. Most preferred are strong inorganic acids, such as hydrochloric, sulfuric or phosphoric acid.

The most preferred compounds are 2-(2-amino-1,6-dihydro-6-oxo-purin-9-yl)methoxy-3-hydroxy-1-propyl L-valinate hydrochloride and acetate. These compounds can be prepared as crystalline materials and therefore can be easily manufactured into stable oral formulations.

In any of the processes described herein, a reference to Formulae I, II, III, IV, V, Va, VI or VII refers to such Formulae wherein R, Z, $P^1$, $P^2$, and A are as defined in their broadest definitions set forth in the Summary of the Invention, with the processes applying particularly to the presently preferred embodiments.

DETAILS OF THE SYNTHETIC PROCESSES

The process of the present invention is depicted in the Reaction Sequence shown below:

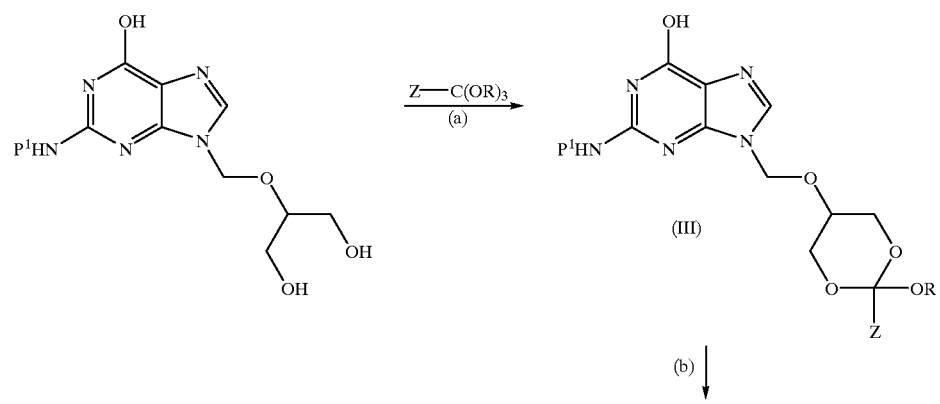

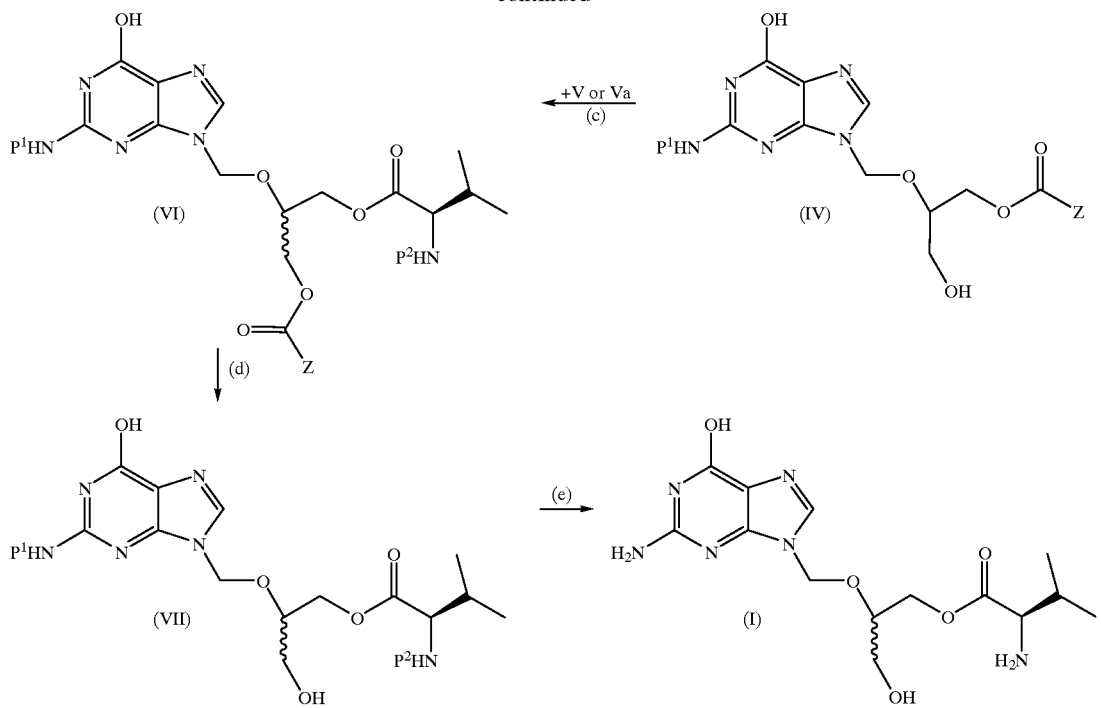

wherein $P^1$ is hydrogen or an amino protecting group, $P^2$ is an amino protecting group, R is lower alkyl, allyl or aralkyl, and Z is hydrogen, lower alkyl, aryl or aralkyl.

Description of Reaction Sequence

The process for the preparation of a compound of Formula (I) comprises:

Step (a): Transesterification of an orthoester of Formula (II), i.e., Z—C(OR)$_3$, wherein R is lower alkyl, allyl or aralkyl, and Z is hydrogen, lower alkyl, aryl or aralkyl, with 2-(2-amino-1,6-dihydro-6-oxo-purin-9-yl)methoxy-1,3-propanediol (ganciclovir) yielding the cyclic orthoester of ganciclovir (Formula (III));

Step (b): Hydrolysis of the cyclic orthoester of Formula (III)) giving ganciclovir monocarboxylate of Formula (IV);

Step (c): Esterification of ganciclovir monocarboxylate of Formula (IV) with an L-valine derivative of Formula (V) or (Va) affording the monocarboxylate-monovalinate of ganciclovir of Formula (VI);

Step (d): Selective hydrolysis of the compound of Formula (VI) under basic conditions or alternatively under enzymatic conditions yielding the monovalinate ganciclovir of Formula (VII); and Step (e): Removal of any protecting groups affording the compound of Formula (I).

Steps (a) through (e) may be carried out as individual steps, that is, the reaction product(s) of each step is/are isolated, purified and identified as necessary.

Alternatively, reaction Steps (a) and (b) or Steps (a) through (c) may be carried out without the discrete isolation of the intermediates obtained in Step (a) or Steps (a) and (b). These "one-pot" reactions may afford a key intermediate compound more quickly and directly. Repetitive and time-consuming isolation and purification procedures are avoided, thereby reducing the overall cost of the processes.

One-pot Reaction for Preparing a Compound of Formula (IV)

Steps (a) and (b)

An orthoester of Formula (II) is transesterified with 2-(2-amino-1,6-dihydro-6-oxo-purin-9-yl)methoxy-1,3-propanediol (ganciclovir) to yield the cyclic orthoester of ganciclovir (Formula III), which is directly hydrolyzed to ganciclovir monocarboxylate (Formula IV).

One-pot Reaction for Preparing a Compound of Formula (VI)

Steps (a), (b) and (c)

An orthoester of Formula (II) is transesterified with 2-(2-amino-1,6-dihydro-6-oxo-purin-9-yl)methoxy-1,3-propanediol (ganciclovir) to yield the cyclic orthoester of ganciclovir (Formula III), which is directly hydrolyzed to ganciclovir monocarboxylate (Formula IV). The ganciclovir monocarboxylate is then esterified with an L-valine derivative of Formula (V) or (Va) to form the compound of Formula (VI), the monocarboxylate-monovalinate of ganciclovir.

In Steps (a) and (b) of the above reaction sequence, the ganciclovir monoalkanoic ester intermediate of Formula (IV) is formed with high selectivity and in high yield. This intermediate allows for mono-esterification by an L-valine derivative (Step c) to provide the monocarboxylate-monovalinate of Formula (VI). The acyl (e.g., alkanoyl or benzoyl) group in this intermediate is then selectively hydrolyzed with base or under enzymatic conditions (Step d) to give the monovaline ester of Formula (VII) in high yield.

Pharmaceutically Acceptable Salts

Compounds of Formula (I) can optionally be converted into a pharmaceutically acceptable salt thereof. This process can also include the conversion of an acid addition salt of the prodrug of Formula (I) into a non-salt form, the optical resolution of a compound of Formula (I) or the preparation of the compound of Formula (I) in crystalline form.

Protection of Amino Groups

The process for producing the compound of Formula (I) may or may not involve protection of the amino group in the 2-position of the guanine base (see the detailed description below of Steps (a) through (c) for the case in which the process is carried out without a protected amino group). For the case when the ganciclovir starting material has a protected 2-amino group the protecting group may be removed by conventional procedures, well-known in the art. For example, if the amino-protecting group is a lower alkanoyl group, basic conditions (pH between 8 to 11) are employed to remove the protecting group. For example, 2-N-acetyl-ganciclovir is treated with an alkaline reagent such as ammonium hydroxide, sodium or potassium carbonate or sodium or potassium hydroxide until the removal of the acetyl group is complete. In general, this reaction will be conducted in the presence of a suitable solvent such as a lower alkanol. Preferably the starting material is dissolved in methanol and a stoichiometric excess of ammonium hydroxide is added. The reaction temperature is kept between 0° C. to 50° C., preferably at room temperature. After the reaction is complete (which can be determined by TLC), another solvent may be added to facilitate isolation of the de-protected product, such as ethyl ether, which leads to precipitation of the de-acylated product which can be isolated using conventional separation methods, e.g., filtration.

Starting Materials

All starting materials employed to make the compound of Formula (I) are known, such as ganciclovir, the orthoesters of Formula (II), and the protecting and carboxylic-group-activating reagents. Prior to carrying out Step (b) (esterification step), the amino group of the L-valine derivative must be protected to avoid its interference with the esterification by undesirable amide formation. The various amino-protected L-valine derivatives useful in this invention, such as N-benzyloxycarbonyl-L-valine, BOC-L-valine and FMOC-L-valine, N-acetyl-L-valine and N-benzyloxycarbonyl-N-carboxy-L-valine anhydride, are all commercially available (SNPE Inc., Princeton, N.J., Aldrich Chemical Co., Milwaukee, Wis., and Sigma Chemical Co., St. Louis, Mo.), or are described in the literature, such as N-allyloxy-carbonyl-L-valine. Cyclic amino-protected L-valine derivatives are also described in the literature, as noted above. Of particular interest for the present invention is the benzyloxycarbonyl valine-substituted 2-oxa-4-aza-cycloalkane-1,3-dione (Z-valine-N-carboxyanhydride, or Z-valine-NCA), which is also commercially available (SNPE Inc., Princeton, N.J.). Alternatively, the protecting step may be carried out by conventional methods.

A preferred ganciclovir starting material for the preparation of the compound of the invention is the unprotected ganciclovir (2-(2-amino-1,6-dihydro-6-oxo-purin-9-yl) methoxy-1,3-propanediol) which is described in U.S. Pat. No. 4,355,032. Other preferred ganciclovir starting materials may have protection at the 2-amino group, such as 2-(2-acyl-amino-1,6-dihydro-6-oxo-purin-9-yl)methoxy-1, 3-propanediol, including 2-(2-trifluoro-acetylamino-1,6-dihydro-6-oxo-purin-9-yl)methoxy-1,3-propanediol, and 2-(2-trichloroacetylamino-1,6-dihydro-6-oxo-purin-9-yl) methoxy-1,3-propanediol, and 2-(2-acetylamino-1,6-dihydro-6-oxo-purin-9-yl)methoxy-1,3-propanediol.

Preparation of Activated Derivative of L-valine:

Prior to carrying out Step (c) (esterification step), L-valine must also be activated. At least 1 equivalent of the protected amino acid and 1 equivalent of a suitable coupling agent or dehydrating agent, for example 1,3-dicyclohexylcarbodiimide or salts of such diimides with basic groups should be employed from the start. Other activators such as N,N'-carbonyl-diimidazole may also be used. Further useful dehydrating agents are trifluoroacetic anhydride, mixed anhydrides, acid chlorides, 1-benzotriazolyloxy-tris(dimethylamino)phosphonium hexafluorophosphate, benzotriazole-1-yl-oxy-trispyrrolidinophosphonium hexafluorophosphate, 1-hydroxybenzotriazole, 1-hydroxy-4-azabenzotriazole, 1-hydroxy-7-azabenzotriazole, N-ethyl-N'-(3-(dimethylamino)propyl)carbodiimide hydrochloride, 3-hydroxy-3,4-dihydro-4-oxo-1,2,3-benzotriazine, O-(benzotriazol-1-yl)-1,1,3,3-tetramethyluronium hexafluorophosphate, O-(7-azabenzotriazol-1-yl)-1,1,3,3-tetramethyluronium hexafluorophosphate, O-(7-azabenzotriazol-1-yl)-1,1,3,3-tetramethyluronium tetrafluoroborate, O-(1H-benzotriazol-1-yl)-1,1,3,3-bis (tetramethylene)uronium hexafluorophosphate, or O-(7-azabenzotriazol-1-yl)-1,1,3,3-bis(tetramethylene)uronium hexafluorophosphate.

A description of these coupling agents by L. A. Carpino can be found in J. Am. Chem. Soc. 1993, 115, p. 4397–4398.

Also useful for this purpose are urethane-protected amino acid N-carboxy anhydrides (UNCAs) which have been described by William D. Fuller et al., J. Am. Chem. Soc. 1990, 112, 7414–7416, which is incorporated herein by reference. Other protected amino acid N-carboxy anhydrides are described in PCT Patent Application WO94/29311, discussed above. In summary, any other reagent that produces an anhydride or another activated derivative of the protected amino acid under mild conditions can be used as the coupling agent.

The amino-protected amino acid is dissolved in an inert solvent such as a halogenated lower alkane, preferably dichloromethane under an inert atmosphere, for example nitrogen, and the coupling agent is added (preferably 1,3-dicyclohexylcarbodiimide). The reaction mixture is stirred at temperatures between 0° C. and 50° C., preferably at about room temperature. The reaction mixture is filtered and the reaction product (the anhydride of the protected amino acid) isolated. The resulting product is dissolved in a dry inert solvent, such as dimethylformamide, and placed under nitrogen.

Preparation of Mono-L-valine Ganciclovir

Step (a): Transesterification

An orthoester of Formula (II), i.e., Z—C(OR)$_3$, where Z is hydrogen, lower alkyl, aryl or aralkyl and R is lower alkyl, allyl or aralkyl, is transesterified with ganciclovir, with the 2-amino group optionally protected, to give the cyclic orthoester of ganciclovir (Formula (III)). Suitable amino-protecting groups are lower alkanoyl groups with 2 to 4 carbon atoms, in particular the acetyl group, especially the trifluoroacetyl and trichloroacetyl groups, and the propionyl group. Other suitable amino-protecting groups are the trityl or substituted trityl groups, such as the monomethoxytrityl group, and the 4,4'-dimethoxytrityl group. Preferred orthoesters are the trimethyl, triethyl and tribenzyl orthoesters. Most preferred are the trimethyl and triethyl orthoacetates and orthopropionates.

To a slurry of ganciclovir and about 3–20 equivalents of orthoester, preferably 2–6 equivalents of orthoester and optionally an inert solvent, preferably a polar solvent such as ethanol, dimethylformamide or dimethylsulfoxide, is added a small amount of an organic acid catalyst such as pyridinium p-toluenesulfonate (PPTS), p-toluenesulfonic acid monohydrate (PTSA), trifluoroacetic acid (TFA), or (1S)-(+)-10-camphorsulfonic acid.

The reaction is carried out at 20°–40° C., preferably at ambient temperature from 1 hour to 4 days, preferably 3–12 hours. Optional isolation of the product is achieved by conventional means such as filtration, followed by washing and drying.

Step (b): Hydrolysis

The product of Step (a), the cyclic orthoester of Formula (III) is converted into the monocarboxylate of Formula (IV) by hydrolysis under either acidic or hydrogenolytic conditions.

Acid Hydrolysis

The cyclic orthoester of Formula (III) obtained in Step (a), wherein R is lower alkyl, allyl or aralkyl, and Z is hydrogen, lower alkyl, aryl or aralkyl, is converted into the monocarboxylate of Formula (IV) by acid hydrolysis, preferably with dilute aqueous acetic acid (or formic acid if the orthoester of Formula (III) is an orthoformate), at a temperature of 10°–80° C., preferably at room temperature to 55° C. A polar solvent such as ethanol, isopropyl acetate or tert-butyl methyl ether (MTBE), is added to the reaction mixture and the slurry is cooled on an ice bath for 0.5 to 2 hours, preferably 1 hour The monoalkanoic ester is collected by filtration, washed and dried under vacuum at ambient temperature.

Hydrogenolysis

Alternatively, when R is aralkyl, e.g., benzyl, the conversion to a compound of Formula (IV) can be done under non-hydrolytic conditions by reacting the compound of Formula (III) where R is benzyl with hydrogen under palladium catalysis, resulting in hydrogenolytic removal of the benzyl group. The hydrogenolysis is preferably carried out by dissolving the orthoester intermediate (III) in a solvent under conventional hydrogenation conditions at 5–100 psi (0.35–7 atm), preferably 10–40 psi (0.7–2.8 atm) hydrogen, in the presence of a catalyst such as a palladium compound, in particular palladium hydroxide on carbon (Pearlman's catalyst), at about 20°–60° C., preferably 20°–35° C., until completion of the reaction. Other suitable catalysts include hydrogenation catalysts in general such as Pd, Pd on carbon and homogeneous hydrogenation catalysts. The solvent system includes aprotic solvents such as dimethylformamide, lower alkanol such as methanol or ethanol. Generally the reaction will be carried out at temperatures between room temperature and the reflux temperature of the solvent system, for example in refluxing ethanol under a hydrogen atmosphere and under exclusion of air. The reaction vessel is preferably swept with nitrogen before charging it with hydrogen.

Step (c): Esterification

In this step, the ganciclovir monocarboxylate intermediate of Formula (IV) obtained in Step (b) is esterified with an activated derivative of amino-protected L-valine of Formula (V) or (Va). Suitable amino-protecting groups for the L-valine derivative are the N-benzyloxycarbonyl (CBZ) group, the tertiary butyloxycarbonyl (t-BOC) group and the N-(9-fluorenyl-methoxycarbonyl) or "FMOC" group. A solution of at least 1 equivalent (preferably 1.2–1.6 equivalents) of the L-valine derivative, preferably valine anhydride or cyclic valine anhydride, most preferably Z-valine-NCA, in an aprotic polar solvent, preferably dimethylformamide is added to a suspension/slurry of ganciclovir monocarboxylate of Formula (IV) obtained in Step (b) in the presence of 4-dimethylaminopyridine at −10° to 20° C., preferably at 5°–15° C. The reaction mixture is allowed to stir at ambient temperature for 1–5 hours, preferably 2–3 hours. To the reaction mixture is added isopropyl acetate. The precipitate is collected by filtration, washed and dried under vacuum at 30°–60° C., preferably 45°–50° C. for 1–3 days, preferably 2 days.

Step (d): Selective Hydrolysis

The acyl (e.g., alkanoyl or benzoyl) group can be removed from the monocarboxylate-monovalinate of Formula (VI) obtained in Step (c) by basic, acidic or enzymatic hydrolysis.

Basic Hydrolysis

Alkanoyl groups such as acetyl, propionyl and butyryl are selectively removed, preferably under basic conditions. For example, the mono-carboxylate-monovalinate of Formula (VI) is mixed with isopropyl acetate/dimethylformamide (5:1 to 10:1) and an equal amount of concentrated ammonium hydroxide is added. The reaction mixture is stirred at 10°–50° C., preferably at ambient temperature for 4–100 hours, preferably 12–24 hours. The reaction mixture is then neutralized with 5% aqueous hydrochloric acid, most of the isopropyl acetate is removed under reduced pressure and the product, a white solid, is collected by filtration.

Acidic Hydrolysis

The formyl group is removed from the monoformate-monovaline ester obtained in Step III preferably by acid hydrolysis. For example, the monoformate-valinate of Formula (VI) is preferably dissolved in methanol/dichloromethane, preferably methanol/dichloromethane 2:1, and an equal amount of dilute aqueous acid, preferably 2M hydrochloric acid, is added. The reaction mixture is stirred at 10°–50°, preferably at ambient temperature for 4–30 hours, preferably 8–16 hours. The methanol/aqueous hydrochloric acid layer is separated, and aqueous ammonium hydroxide is added until the pH of the solution is 5–6, preferably 5.5. The solid product is collected by filtration, washed and dried under vacuum at 40°–60°, preferably at 50°–55° for 20 to 60 hours, preferably about 40 hours.

Enzymatic Hydrolysis

Alternatively, the acyl (e.g., alkanoyl or phenylacetyl) group can be removed by enzymatic hydrolysis. For example, the monocarboxylate-monovalinate of Formula (VI), obtained in Step (c), is added to propylene glycol/0.2 M phosphate buffer. To the suspension is added either a crude enzyme preparation such as Amano AK, available from Amano International, or preferably a purified enzyme preparation, such as Chiro-CLEC® PC suspension, a pseudomonas species lipase preparation, available from Altus Biologics Inc. This mixture is incubated in a rotary shaker at 100 to 400 rpm, preferably 200–300 rpm for 3 to 30 days, preferably for 12–16 days, at RT to 50° C., preferably about 35°–40° C. The pH is maintained at 6–8 by adding 5% NaOH as necessary. The monovalinate product is isolated by filtration and dried. Further purification can be accomplished by preparative thin layer chromatography or column chromatography. Other cosolvents, such as methanol, polyethyleneglycol (MW 200 or 400) can also be used.

Step (e): Final De-protection to Give the Product of Formula (I)

The valine amino-protecting group in the product of step (d) (Formula (VII)) is removed by a de-protection reaction, preferably in an acidic medium or solvent. For example, for the benzyloxycarbonyl (i.e., carbobenzyloxy=CBZ group) hydrogenolysis is preferred. De-protection under acidic conditions is preferred, as this will ensure that the amino group liberated in the de-protection reaction will be protonated; that is, the free amino group as it is formed in the de-protection reaction will be captured by an at least stoichiometric amount of acid present. Isolating the compound of Formula (I) as an acid addition salt will protect the desired stereoconfiguration of the compound of Formula (I). Therefore, those examples given below that show the de-protection step also show the concomitant salt formation step.

The de-protection reaction is carried out by dissolving the product of Step (d) in an inert solvent, preferably in an acidic solvent, using a hydrogenation catalyst, such as palladium hydroxide on carbon, palladium on carbon or platinum, using elevated hydrogen pressure between 1 and 2000 psi (0.1–140 atm), preferably 5 to 200 psi (0.3–14 atm). Preferably, the inert solvent is a polar solvent, most preferably methanol, containing aqueous 2–12M hydrochloric acid. The hydrogenation is carried out at 5–20 psi (0.3–1.4 atm), preferably 6–8 psi (0.4–0.6 atm) in the presence of palladium hydroxide on carbon (Pearlman's catalyst) at ambient temperature for 2–48 hours, preferably 16–24 hours. After completion of the reaction, the catalyst is removed by filtration and the solution is concentrated under reduced pressure. Crystallization yields the desired product as the hydrochloride salt. If present, any protecting group at the 2-amino group of the guanine moiety may be removed by conventional procedures, as described above.

If the tertiary butyloxycarbonyl (t-BOC) group is being used as amino-protecting group, its removal is effected with acid, such as HCl and isopropanol as solvent or with trifluoroacetic acid as solvent and acid. Alternatively, if the esterification step has been carried out with a trityl or substituted trityl-protected ganciclovir derivative, such protecting groups can be removed by treatment with an aqueous alkanoic acid, for example aqueous acetic or trifluoroacetic acid, or hydrochloric acid at temperatures between –20° C. and 100° C.

Preparation of Intermediate of Formula (IV)

One Pot Reaction, Steps (a) and (b)

To a slurry of ganciclovir and about 3–30 equivalents of orthoester of Formula (II), preferably 4–8 equivalents of orthoester of Formula (II) and optionally an inert solvent, preferably a polar solvent such as ethanol, dimethylformamide or dimethylsulfoxide, is added a small amount of an organic acid catalyst such as pyridinium p-toluenesulfonate (PPTS) or p-toluenesulfonic acid monohydrate (PTSA). The reaction is carried out at 20°–40° C., preferably at ambient temperature from 1–48 hours, preferably 3–6 hours. Water is added (about 100–1000 equivalents, preferably 200–400 equivalents) and the slurry is stirred for 0.5 to 3 hours, preferably 0.5 to 1 hour. Excess orthoester reagent is then removed by distillation under vacuum (aspirator). To the resulting slurry is added about 100–1000 equivalents, preferably 200–400 equivalents of isopropyl acetate. The mixture is stirred for about 10–100 min, preferably 15–30 min, and then filtered and washed with isopropyl acetate. The product, a compound of Formula (IV), is dried under vacuum at 30°–60° C., preferably 45°–50° C. for 1–2 days, preferably 1 day.

Preparation of Intermediate of Formula (VI)

One Pot Reaction, Steps (a), (b) and (c)

To a slurry of ganciclovir and about 3–30 equivalents of orthoester of Formula (II), preferably 4–8 equivalents of orthoester of Formula (II) and optionally an inert solvent, preferably a polar solvent such as ethanol, dimethylformamide or dimethylsulfoxide, is added a small amount of an organic acid catalyst such as pyridinium p-toluenesulfonate (PPTS) or p-toluenesulfonic acid monohydrate (PTSA). The reaction is carried out at 20°–40° C., preferably at ambient temperature from 1–48 hours, preferably 3–6 hours. Water is added (about 100–1000 equivalents, preferably 200–400 equivalents) and the slurry is stirred for 0.5 to 3 hours, preferably 1 to 2 hours. About 200–2000 equivalents, preferably 1000–1500 equivalents of isopropyl acetate is then added to the slurry. The mixture is vacuum distilled at about 100–200 mm (Hg) of pressure until the volume has been largely reduced. To the concentrated mixture is added about 1–2 equivalents, preferably 1.2–1.5 equivalents of Z-valine-NCA and a catalytic amount of DMAP (4-dimethylaminopyridine). The reaction mixture is stirred at room temperature and the progress of the reaction is followed by HPLC. When the reaction is essentially complete, about 1000–1500 equivalents of isopropyl acetate is added and the reaction mixture is heated to 40° to 60° C., preferably to 50°–55° C. for 20 to 100 min, preferably 20 to 40 min. The reaction mixture is then allowed to cool to room temperature and stirred for 5–24 hours, preferably 10 to 15 hours. The product, a compound of Formula (VI), is collected by filtration, washed with isopropyl acetate and dried under vacuum at about 40° to 60° C. for 1 to 2 days, preferably 1 day.

Preparation of Salts

One of ordinary skill in the art will also recognize that the compound of Formula (I) may be prepared as an acid addition salt or as the corresponding free base. If prepared as an acid addition salt, the compound can be converted to the free base by treatment with a suitable base such as ammonium hydroxide solution, sodium hydroxide, potassium hydroxide or the like. However, it is important to point out that the free base of Formula (I) is more difficult to characterize than its acid addition salts. When converting the free base to an acid addition salt, the compound is reacted with a suitable organic or inorganic acid (described earlier). These reactions are effected by treatment with an at least stoichiometric amount of an appropriate acid (in case of the preparation of an acid addition salt) or base (in case of liberation of the free base of Formula (I)). In the salt-forming step of this invention, typically, the free base is dissolved in a polar solvent such as water or a lower alkanol (preferably isopropanol) and mixtures thereof and the acid is added in the required amount in water or in lower alkanol. The reaction temperature is usually kept at about 0° C. to, preferably, about room temperature. The corresponding salt precipitates spontaneously or can be brought out of solution by the addition of a less polar solvent, removal of the solvent by evaporation under reduced pressure, or by cooling the solution.

Isolation of Stereoisomers and Preparation of Crystalline 2-(2-Amino-1,6-dihydro-6-oxo-purin-9-yl)methoxy-3-hydroxy-1-propyl-L-valinate From Formula (I) it is apparent that the compound of the invention has one asymmetric carbon atom (chiral center) in the propyl chain, in addition to the asymmetric carbon atom in L-valine. Therefore, two diastereomeric forms exist, the (R) and (S) forms as determined by the rules of Cahn et al. Suitable methods for the separation of the diastereomers are described in EP A 0694 547.

The compounds of Formula (I) may also be prepared in crystalline form, which has many well-known advantages over the non-crystalline form. Suitable methods for the preparation of the compounds of the invention in crystalline form are also described in EP A 0694 547, incorporated herein by reference.

The following preparations and examples are given to enable those skilled in the art to more clearly understand and to practice the present invention. They should not be considered as limiting the scope of the invention, but merely as being illustrative and representative thereof.

EXAMPLE 1

Preparation of Intermediates of Formula (III)

1A. Preparation of 2-(2-Amino-1,6-dihydro-6-oxo-purin-9-yl)methoxy-1,3-propyl-methyl orthoformate To 500 g of 2-(2-Amino-1,6-dihydro-6-oxo-purin-9-yl) methoxy-1,3-propanediol (ganciclovir) was added a premixed solution of 1 L dimethylformamide, 0.5 L trimethyl orthoformate, and 0.18 L trifluoroacetic acid (TFA). The reaction mixture was stirred for five days. An additional premixed solution of 0.667 L dimethylformamide, 0.333 L trimethyl orthoformate, and 41 ml TFA was added. The reaction mixture was stirred for an additional five days. Solid material was filtered out and washed with ca. 2.5 L of 10% trimethyl orthoformate in ethyl acetate. The solid was dried in a vacuum oven at 25 ins Hg (ca. 635 torr), (nitrogen sweep, room temperature) for 3 days. Weight of solid: 557 g. HPLC: 3.4% ganciclovir, >90% orthoformate ester; MS: 298 (MH)+

1B. Preparation of 2-(2-Amino-1,6-dihydro-6-oxo-purin-9-yl)methoxy-1,3-propyl-benzyl orthoformate Alternatively, the benzyl orthoformate ester was prepared as follows: To a suspension of ganciclovir (5 g) in dimethylformamide (50 ml) was added tribenzyl orthoformate (20 g), and (1S)-(+)-10-camphorsulfonic acid (4 g). The reaction mixture was stirred at room temperature overnight, and then added to a two phase mixture of a solution of sodium bicarbonate (1.4 g) in water (75 ml) and hexane (25 ml). After stirring, the mixture was filtered, washed with hexane and dried under vacuum to give 7.1 g of material (comparable by HPLC to the product obtained in Example 1A). MS: 374 (MH)+.

1C. Preparation of 2-(2-Amino-1,6-dihydro-6-oxo-purin-9-yl)methoxy-1,3-propyl-ethyl orthoacetate To 5 g of 2-(2-amino-1,6-dihydro-6-oxo-purin-9-yl)methoxy-1,3-propanediol (ganciclovir) in 20 ml of triethyl orthoacetate and 10 ml of ethanol was added 5 ml of dimethylsulfoxide (DMSO) and 0.15 g of pyridinium p-toluenesulfonate (PPTS). The slurry was stirred at room temperature for 3.5 hours and then filtered. The white solid was washed twice with 50 ml each of diethyl ether then air dried to give 5.92 g of product. $^1$H-NMR: δ 1.6 (t,3H), 2.0 (s,3H), 3.55 (m,3H), 4.0 (d,2H), 4.2 (q,2H), 5.5 (s,2H), 8.05 (s,1H), aa 8.5 (s,1H).

Alternatively, the orthoacetate is not isolated and the slurry is used as is for the hydrolysis step to give the monoacetate (Example 2B).

EXAMPLE 2

Preparation of Intermediates of Formula (IV)

2A. Preparation of 2-(2-Amino-1,6-dihydro-6-oxo-purin-9-yl)methoxy-3-formyloxy-1-propanol To a solution of 1.25 L 95–97% formic acid, 300 ml dimethylformamide and 50 ml water, at 45° C., was added 557 g of the methyl orthoformate ester (from Example 1A) and slurried in 2 L dimethylformamide in portions over 20 minutes. The reaction temperature rose to 54° C. After 45 minutes of agitation the reaction was complete by HPLC. After 1 hour and 45 minutes of mixing the reaction mixture was poured into 15 L tert-butyl methyl ether (MTBE). The solid was filtered out of solution and then washed with 5 L of MTBE. The solid was dried in a vacuum oven at ca. 25 ins of Hg (ca. 635 torr), nitrogen sweep, room temperature, for 2 days. Mass of solid: 478 g. HPLC: 68% monoformate of ganciclovir, 14.8% ganciclovir.

2B. Alternatively, the monoformate of ganciclovir can be prepared from the benzyl orthoformate ester of gancyclovir (from Example 1B).

A 200 ml Parr bomb was charged with 10 g benzyl orthoformate ester of ganciclovir, (37% water by the Karl Fisher test), 3 g Pearlman's catalyst, and 50 ml dimethylformamide. The reaction mixture was left under 35 psi (2.5 atm) hydrogen overnight. The following morning the progress of the reaction was checked by HPLC. The reaction mixture contained 19% starting material. The solid was rinsed off the walls of the Parr bomb with dimethylformamide and the reaction mixture was placed under 35 psi (2.5 atm) hydrogen overnight. The following morning the reaction was complete by HPLC. The catalyst was filtered out of the reaction mixture over a Solka Floc bed, and the bed rinsed with dimethylformamide (final volume of DMF about 225 ml). The product was not isolated, but used directly in the next reaction step (Example 3B).

2C. Preparation of 2-(2-Amino-1,6-dihydro-6-oxo-purin-9-yl)methoxy-3-acetoxy-1-propanol A slurry of 5.92 g of ethyl orthoacetate of ganciclovir (from Example 1A) and 50 ml of 70% aqueous acetic acid was stirred at room temperature for 2 hours. 50 ml of ethanol was added and the thick slurry was cooled in an ice bath for 1 hour. The reaction mixture was then filtered and washed twice with 50 ml of ethanol. The white solid was dried in a vacuum oven at ca. 500 mm of Hg (torr), (nitrogen sweep, 60° C.) to give 5.1 g of the monoacetate of ganciclovir.

2D. Preparation of 2-(2-amino-1,6-dihydro-6-oxo-purin-9-yl)methoxy-3-acetoxy-1-propanol from Ganciclovir One-pot procedure, Steps (a) and (b)

To a slurry of 5 g of ganciclovir in 15 ml of trimethylorthoacetate and 5 ml of DMSO was added 0.15 g of p-toluenesulfonic acid dihydrate (PTSA). The mixture was stirred for 4 hours at room temperature. 5 ml of tap water was then added to the reaction mixture and stirring was continued for an additional 45 min. The slurry was distilled under vacuum (aspirator) to remove excess trimethyl orthoacetate and methanol. To the resulting slurry was added 30 ml of isopropyl acetate and the mixture was stirred for 20 min. The reaction mixture was then filtered and washed twice with 5 ml of isopropyl acetate. The white solid was dried in a vacuum oven at ca. 500 mm of Hg (torr), nitrogen sweep, 60° C.) overnight to give 5.06 g of the monoacetate of ganciclovir. $^1$H-NMR: δ 1.8 (s,3H), 3.35 (m,2H), 3.75 (m,1H), 3.85 (dd,1H), 4.05 (dd,1H), 4.8 (t,1H), 5.35 (ab, 2H), 6.45 (br s,2H), 7.75 (s,1H), 10.6 s,1H).

2E. Preparation of 2-(2-Amino-1,6-dihydro-6-oxo-purin-9-yl)methoxy-3-propionyloxy-1-propanol One-pot procedure, Steps (a) and (b)

To 5 g of 2-(2-amino-1,6-dihydro-6-oxo-purin-9-yl)methoxy-1,3-propanediol (ganciclovir) in 20 ml of triethyl orthopropionate was added 5 ml of dimethylsulfoxide (DMSO) and 0.25 g of pyridinium p-toluenesulfonate (PPTS). The slurry was stirred at room temperature for 4.5 hours. 70% Aqueous acetic acid (10 ml) was added and the mixture was stirred for 2 hours. Then 30 ml of ethanol was added, the mixture was stirred for another 0.5 hour and filtered. The white solid was washed twice with 50 ml each of ethanol and air dried to give 4.77 g of product. $^1$H-NMR: δ 0.9 (t,3H), 2.05 (q,2H), 3.32 (m,2H), 3.8 (m,1H), 3.85 (dd,1H), 4.0 (dd,1H), 4.8 (t,1H), 5.35 (ad,2H), 6.45 (br s, 2H), 7.75 (s,1H), 10.6 (s,1H).

EXAMPLE 3

Preparation of Intermediates of Formula (VI)

3A. Preparation of 2-(2-Amino-1,6-dihydro-6-oxo-purin-9-yl)methoxy-3-formyloxy-1-propyl-N-(benzyloxycarbonyl)-L-valinate To 472 g of monoformate of ganciclovir (from Example 2A) in 1.42 L dimethylformamide was added 75.5 ml TEA. The above mixture was cooled to 10°–15° C. and then 601 g of Z-valine-NCA (1.4 equivalents) dissolved in 600 ml dimethylformamide was added over one hour. The reaction was complete by HPLC in 2 hours. The reaction mixture was added dropwise to 12 L of water. The solid was filtered out and washed with 8 L water. The solid was dried in a vacuum oven at ca. 25 ins of Hg (ca 635 torr), nitrogen sweep, 60° C., for 2 days. Mass: 838 g. HPLC analysis: 68% Z-valine-monoformate of ganciclovir, 14% bis-Z-valinate, 1.2% ganciclovir.

3B. In a like manner, the reaction product of Example 2B was coupled with Z-valine-NCA to yield 5.31 g or Z-valine-monoformate of ganciclovir (HPLC analysis: 74%).

3C. Preparation of 2-(2-Amino-1,6-dihydro-6-oxo-purin-9-yl)methoxy-3-acetoxy-1-propyl-N-(benzyloxycarbonyl)-L-valinate from Ganciclovir To a solution of 4.0 g of the monoacetate of ganciclovir in 5 ml of isopropyl acetate and 5 ml of dimethylformamide was added 4.1 g of Z-valine-NCA and 0.08 g of 4-dimethylaminopyridine (DMAP). The solution was stirred for 3 hours at room temperature. An additional 0.8 g of Z-valine-NCA was added and stirring was continued for 1 hour. The solution was drowned with 75 ml of isopropyl acetate and stirred for 3 hours. The reaction mixture was then filtered and washed twice with 10 ml each of isopropyl acetate. The product was dried in a vacuum oven at ca. 500 mm of Hg (torr), (nitrogen sweep, 60°) overnight to give 5.6 g of Z-valine-ganciclovir monoacetate.

3D. Preparation of 2-(2-Amino-1,6-dihydro-6-oxo-purin-9-yl)methoxy-3-propionyloxy-1-N-(benzyloxycarbonyl)-L-valinate from Ganciclovir To a solution of 2.0 g of monopropionate of ganciclovir in 10 ml of dimethylformamide was added 2.0 g of CBZ-valine-NCA and 0.05 g of 4-di-methylaminopyridine (DMAP). The slurry was stirred for 4 hours at room temperature. An additional 0.21 g of CBZ-valine-NCA was added and stirring was continued for 1 hour. An additional 0.1 g of CBZ-valine-NCA was added and the mixture was stirred for another hour. The solution was drowned with 50 ml of diethyl ether and stirred for 0.5 hour. The reaction mixture was filtered, the solid was washed twice with 20 ml each of diethyl ether and air-dried to give 3.54 g of Z-valine-ganciclovir monopropionate. $^1$H-NMR (diastereomeric mixture): δ 0.85 (two d, 6H), 0.95 (t,3H), 1.9 (m,1H), 2.1 (m,2H), 4.05 (m,6H), 5.0 (s,2H), 5.4 (s,2H), 6.5 (br s,2H), 7.35 (m,5H), 7.65 (two d,1H), 7.75 (two s,1H), 10.65 (s,1H).

3E. Preparation of 2-(2-Amino-1,6-dihydro-6-oxo-purin-9-yl)methoxy-3-acetoxy-1-propyl-N-(benzyloxycarbonyl)-L-valinate from Ganciclovir One-pot preparation, Steps (a), (b) and (c)

To a slurry of 5 g of ganciclovir in 10 ml of trimethyl orthoacetate and 10 ml of dimethylformamide was added 0.2 g of pyridinium p-toluene-sulfonate (PPTS). The slurry was stirred at room temperature overnight. Then 5 ml of tap water was added to the thick white slurry and stirring was continued for 1.5 hours. 150 ml of isopropyl acetate was added to the reaction mixture. The mixture was then vacuum distilled at approximately 100–150 mm of Hg (torr) until the volume was about 20 ml. To the concentrate was then added 7.0 g of Z-valine-NCA and 0.2 g of 4-dimethylaminopyridine (DMAP). The mixture was stirred until all the solid had dissolved. The reaction was followed by HPLC. An additional 0.5 g of Z-valine-NCA was needed to complete the process. Then 150 ml of isopropyl acetate was added and the mixture was heated to 50°–55° C. for 30 min. The mixture was allowed to cool slowly and stirred overnight with very slow agitation. The slurry was filtered and washed twice with 10 ml each of isopropyl acetate. The white solid was dried in a vacuum oven at ca. 500 mm of Hg (torr), (nitrogen sweep, 60°) to give 7.82 g of Z-valine-ganciclovir monoacetate. HPLC analysis: 94% Z-valine-ganciclovir monoacetate, 0.8% bis-Z-valinate. $^1$H-NMR (diastereomeric mixture): δ 0.8 (two d,6H), 1.8 (two s,3H), 1.9 (m,1H), 3.95 (m,6H), 5.0 (s,2H), 5.4 (s,2H), 6.5 (s,2H), 7.3 (m,5H), 7.7 (two d,1H), 7.8 (s,1H), 10.6 (s,1H).

EXAMPLE 4

Preparation of Intermediates of Formula (VII)

4A. Preparation of 2-(2-Amino-1,6-dihydro-6-oxo-purin-9-yl)methoxy-3-hydroxy-1-propyl-N-(benzyloxycarbonyl)-L-valinate To 778 g of Z-valine-monoformate of ganciclovir was added 780 ml methanol, 780 ml 2M HCl, and 390 ml dichloromethane. This mixture was stirred overnight. The following morning the reaction was complete by HPLC. To this was added 500 ml methanol, 500 ml 3 M HCl, and 250 ml dichloromethane. The dichloromethane layer was separated, and the methanol/HCl layer was washed with 200 ml dichloromethane. The dichloromethane wash was combined with the dichloromethane layer. The dichloromethane layer was extracted three times with 1 L methanol: 1.5 L 3 M HCl. Each time the methanol/HCl layer was washed with 200 ml dichloromethane to remove residual bis-Z-valinate. The dichloromethane wash was then combined with the dichloromethane layer for further methanol/HCl extractions following the above procedure. The final level of Z-valine-ganciclovir in dichloromethane layer was 4.2% by HPLC. The methanol/HCl layers were combined, cooled to 19° C. in an ice/water bath, and then 1.94 L of aqueous NH$_4$OH was added to bring the pH to 5.5. The temperature rose to about 25° C. The mixture was aged 1 hour at ~10° C. The solid was filtered out, washed with 8 L ~40° C. water and then dried in a vacuum oven at ca. 700 millimeters of Hg (torr), (nitrogen sweep, 55° C.) for 38.5 hours. Weight of Z-valine-ganciclovir 486 g. HPLC analysis: 96.2% Z-valine-ganciclovir, 1.7% ganciclovir, 1.9% bis-Z-valinate.

4B. Preparation of 2-(2-Amino-1,6-dihydro-6-oxo-purin-9-yl)methoxy-3-hydroxy-1-propyl-N-(benzyloxycarbonyl)-L-valinate To 1.0 g of Z-valine-monoacetate of ganciclovir was added 10 ml of isopropyl acetate, 1 ml of conc. NH$_4$OH (28%), and 1 ml of dimethylformamide. This mixture was stirred at room temperature overnight. The following morning HPLC showed 70.4% mono-Z-valinate, 21% ganciclovir and 6.8% acetate valinate. To this was added 5% aqueous HCl, and the reaction mixture was neutralized to pH ~6.7. Most of the isopropyl acetate was removed under reduced pressure leaving a white solid in aqueous dimethylformamide/isopropyl acetate. The mixture was filtered, washed with water and then dried in a vacuum oven at ca. 500 mm of Hg (torr), (nitrogen sweep, 60° C.) overnight. Yield: 0.699 g. HPLC analysis: 83.7% ganciclovir mono-Z-valinate, 8.5% ganciclovir, 7.2% ganciclovir acetate.

4C. Preparation of 2-(2-Amino-1,6-dihydro-6-oxo-purin-9-yl)methoxy-3-hydroxy-1-propyl-N-(benzyloxycarbonyl)-L-valinate Enzymatic Hydrolysis of 2-(2-Amino-1,6-dihydro-6-oxo-purin-9-yl)methoxy-3-acetoxy-1-propyl-N-(benzyloxycarbonyl)-L-valinate To 1 g of 2-(2-amino-1,6-dihydro-6-oxo-purin-9-yl) methoxy-3-acetoxy-1-propyl-N-(benzyloxycarbonyl)-L-valinate was added 3.0 ml of propylene glycol and 7.0 ml of 0.2M phosphate buffer (pH~6.8). To the resulting suspension was added 600 microliters of Chiro-CLEC® PC (Altus Biologics Inc.) suspension. The mixture was incubated in a rotary shaker at 250 rpm for 2 weeks at 40° C. with occasional additions of 5% aqueous NaOH to maintain the pH at ~6.8. An HPLC assay showed 93% 2-(2-amino-1,6-dihydro-6-oxo-purin-9-yl)methoxy-3-hydroxy-1-propyl-N-

(benzyloxycarbonyl)-L-valinate, 4% residual 2-(2-amino-1,6-dihydro-6-oxo-purin-9-yl)methoxy-3-acetoxy-1-propyl-N-(benzyloxycarbonyl)-L-valinate and 3% 2-(2-amino-1,6-dihydro-6-oxo-purin-9-yl)methoxy-1,3-propanediol (ganciclovir). The product of Formula (VII) was isolated by addition of 10 ml of tetrahydrofuran to dissolve the product, filtration to remove the catalyst, removal of the tetrahydrofuran and subsequent filtration to collect the product. The product was 94% 2-(2-amino-1,6-dihydro-6-oxo-purin-9-yl) methoxy-3-hydroxy-1-propyl-N-(benzyloxycarbonyl)-L-valinate, 3% residual 2-(2-amino-1,6-dihydro-6-oxo-purin-9-yl)methoxy-3-acetoxy-1-propyl-N-(benzyloxy-carbonyl)-L-valinate and 1% 2-(2-amino-1,6-dihydro-6-oxo-purin-9-yl)-methoxy-1,3-propanediol (ganciclovir). Mp 166–168° C. (softens at 163° C.); $^1$H-NMR: 0.77 (d,3H), 0.79 (d,3H), 1.89 (m,1H), 3.35 (m,2H), 3.7–4.0 (m,3H), 4.17 (2dd,1H), 4.84 (2t,1H), 5.01 (s,2H), 5.39 (s,2H), 6.47 (br s,2H), 7.27 (m,5H), 7.62 (2d,1H), 7.78 (2s,1H), 10.63 (br s,1H); $^{13}$C-NMR: 17.97, 18.92, 29.62, 59.60, 59.68, 60.24, 60.37, 63.51, 63.99, 65.59, 71.08, 71.29, 76.59, 76.84, 116.53, 116.55, 127.77, 127.82, 128.33, 136.91, 137.55, 151.32, 153.88, 156.40, 156.80, 171.68, 171.70.

EXAMPLE 5

Preparation of Compounds of Formula (I)

5A. Preparation of 2-(2-Amino-1,6-dihydro-6-oxo-purin-9-yl)methoxy-3-hydroxy-1-propyl-L-valinate hydrochloride 2.5 g Pearlman's catalyst was pre-reduced in 250 ml methanol under 7 psi (0.5 atm) hydrogen overnight. 50.3 g of N$^\alpha$-Z-valine-ganciclovir was dissolved in 250 ml methanol and 10.3 ml 12M HCl, and added to the above pre-reduced catalyst. This reaction mixture was placed under 7 psi (0.5 atm) hydrogen. The hydrogen atmosphere was replaced with a fresh charge of hydrogen after 45 minutes to remove any carbon dioxide produced during the hydrogenolysis. After 3.5 hours the reaction was complete by TLC (acetonitrile/water/acetic acid=10/1/1.) The catalyst was filtered out on a Solka Floc bed, and the bed washed with 500 ml hot methanol. The methanol was removed under reduced pressure at 50° C. and the residue stored in the freezer overnight. The following morning the residue was dissolved in 40 ml water at 55° C. and 160 ml of isopropyl alcohol was added dropwise to this aqueous solution at 50°–55° C. The mixture allowed to cool slowly to 30° C. This mixture was seeded at 47° C. with mono-L-valine ganciclovir (2-(2-amino-1,6-dihydro-6-oxo-purin-9-yl)methoxy-3-hydroxy-1-propyl-L-valinate hydrochloride) crystals. Crystals formed at 40° C. To this was added 120 ml isopropyl alcohol dropwise at 30° C. The reaction mixture was cooled to 0° C., and aged 2 hours. The mixture was cooled again to –5° C. and crystals were filtered out. The crystals were washed with 150 ml cold 5% water in isopropyl alcohol and then 300 ml cold isopropyl alcohol. The crystals were dried in a vacuum oven at ca. 25 ins of Hg (ca 635 torr), nitrogen sweep, 50° C., for 1 day. Weight of solid: 35.8 g. HPLC: 98.1% mono-L-valine ganciclovir, 1.9% ganciclovir; MS: 355 (MH)+.

5B. Preparation of 2-(2-Amino-1,6-dihydro-6-oxo-purin-9-yl)methoxy-3-hydroxy-1-propyl-L-valinate The compound of Formula (I) may also be prepared from the benzyl orthoformate ester of ganciclovir of Example 1B without the discrete isolation of the monoformate intermediates as follows: 3 g of Pearlman's catalyst was dried by washing it with 100 ml absolute ethanol and then drying it in a vacuum oven at ca. 25 ins of Hg (ca. 635 torr), nitrogen sweep, room temperature, for 4 days. The catalyst was pre-reduced in a 200 ml Parr bomb, 30 ml THF, 35 psi (2.5 atm) hydrogen overnight. A slurry of 10 g of benzyl orthoformate ester of ganciclovir in 80 ml dimethylformamide was added to the above pre-reduced catalyst. The Parr bomb was placed under 35 psi (2.5 atm) hydrogen for 48 hours. The reaction progress was checked by HPLC (52% benzyl orthoformate starting material remained). The bomb was placed back under 70 psi (5 atm) hydrogen and left with agitation for 4 days. HPLC of the reaction mixture showed 22% starting material. The bomb was again placed under 70 psi (5 atm) hydrogen at 30° C. for 7 days. HPLC of the reaction mixture showed 2.8% starting material, 76.1% monoformate of ganciclovir, and 6.9% ganciclovir were present. The reaction mixture was transferred to a 500 ml Erlenmeyer flask, total volume 125 ml. 95 ml ethyl acetate was added and the mixture was stirred for 20 minutes. The catalyst was then filtered out of the reaction mixture over a Solka Floc bed. The ethyl acetate was removed from the dimethylformamide solution by rotary evaporation at 40° C. and 28 ins of Hg (ca. 710 torr).

To the resulting dimethylformamide/monoformate solution was added 1.7 ml TEA and 12.4 g N$^\alpha$-Z-valine-NCA. After one hour and 40 minutes an HPLC analysis of this reaction mixture showed the coupling to be complete , with 0.5% monoformate of ganciclovir remaining unreacted (HPLC). To this N$^\alpha$-Z-valine-monoformate ganciclovir/dimethylformamide solution was added 20 ml 2M HCl, pH 0–2. The reaction mixture was allowed to stir overnight. HPLC showed 14.9% Z-valine-monoformate-ganciclovir remaining. An additional 10 ml 2 M HCl was added and the reaction mixture was allowed to stir for 36 hours. HPLC showed 1.3% Z-valine-monoformate of ganciclovir remained. The mixture was cooled in a ice water bath. The pH of the mixture was adjusted to 4–5 with aqueous NH$_4$OH (10 ml). Approximately ⅔ of the dimethylformamide was removed under reduced pressure at a bath temperature of about 50° C. To the resulting dimethylformamide/Z-valine-ganciclovir solution was added 800 ml water. A white solid formed. This mixture was cooled in an ice water bath. The solid was filtered out, washed with 100 ml of water and dried in a vacuum oven at ca. 25 ins of Hg (ca. 635 torr), ca. 50° C., nitrogen sweep, overnight. Yield: 9.80 g. HPLC: 83.7% Z-valine-ganciclovir (R.T. 29.9 min.), 0.7% ganciclovir (R.T. 8.1 min.), 11.1% bisvalinate of ganciclovir (R.T. 47.1 min.)

5C. Preparation of 2-(2-Amino-1,6-dihydro-6-oxo-purin-9-yl)methoxy-3-hydroxy-1-propyl-L-valinate Hydrochloride 2.29 g Pearlman's catalyst was pre-reduced in 200 ml methanol under 7 psi (0.5 atm) hydrogen overnight. 40 g of N$^\alpha$-Z-valine-ganciclovir was dissolved in 250 ml methanol and 9.4 ml 12M HCl, and added to the above pre-reduced catalyst. The reaction mixture was placed under 7 psi (0.5 atm) hydrogen. The hydrogen atmosphere was replaced with a fresh charge of hydrogen after 45 minutes to remove any carbon dioxide produced during the hydrogenolysis. After 3 hours the reaction was complete by TLC (acetonitrile/water/acetic acid=10/1/1.) The catalyst was filtered out on a Solka Floc bed, and the bed was washed with 500 ml hot methanol. The methanol was removed under reduced pressure at 55° C. The residue was dissolved in 35 ml of water at 55° C. Isopropyl alcohol (140 ml) was added dropwise to the aqueous solution at 50°–55° C. The mixture was allowed to cool slowly to 30° C. Crystals formed after about an hour. More isopropyl alcohol (105 ml) was added dropwise at 30° C. The mixture was allowed to stir overnight and was then cooled to 5° C. The crystals were filtered out and washed with 150 ml cold isopropyl alcohol containing 5% water and then 300 ml cold isopropyl alcohol. The crystals were dried in a vacuum oven at ca. 600 mm of Hg (torr), nitrogen sweep, 50° C.) for 1 day. Weight of solid: 30.25 g. HPLC analysis: 96.4% mono-L-valine ganciclovir, 0.5% bis-Z-valinate; MS: 355 (MH)+.

What is claimed is:

1. A compound of Formula (III)

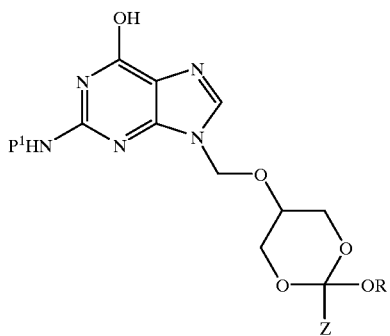

wherein $P^1$ is hydrogen or an amino-protecting group, R is lower alkyl, allyl or aralkyl, and Z is hydrogen, lower alkyl, aryl or aralkyl.

2. A compound of Formula (VI)

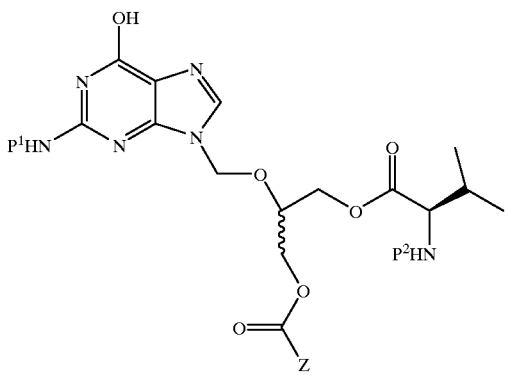

wherein $P^1$ is hydrogen or an amino-protecting group, $P^2$ is an amino protecting group, and Z is hydrogen, lower alkyl, aryl or aralkyl.

* * * * *